(12) United States Patent
Choi

(10) Patent No.: US 11,351,219 B1
(45) Date of Patent: Jun. 7, 2022

(54) FUNCTIONAL FOOD COMPOSITION FOR IMPROVING MUSCULAR ENDURANCE AND RELIEVING FATIGUE

(71) Applicant: Young Jin Choi, Seoul (KR)

(72) Inventor: Young Jin Choi, Seoul (KR)

(*) Notice: Subject to any disclaimer, the term of this patent is extended or adjusted under 35 U.S.C. 154(b) by 0 days.

(21) Appl. No.: 17/540,758

(22) Filed: Dec. 2, 2021

(30) Foreign Application Priority Data

Feb. 10, 2021 (KR) .................. 10-2021-0018837

(51) Int. Cl.
*A61K 36/65* (2006.01)
*A61K 36/481* (2006.01)
*A61K 36/346* (2006.01)
*A61K 36/234* (2006.01)
*A61K 35/32* (2015.01)
*A61K 36/232* (2006.01)

(52) U.S. Cl.
CPC .............. *A61K 36/65* (2013.01); *A61K 35/32* (2013.01); *A61K 36/232* (2013.01); *A61K 36/234* (2013.01); *A61K 36/346* (2013.01); *A61K 36/481* (2013.01); *A23V 2200/30* (2013.01)

(58) Field of Classification Search
None
See application file for complete search history.

(56) References Cited

U.S. PATENT DOCUMENTS

2022/0023364 A1* 1/2022 Kim .................. A61K 36/65

FOREIGN PATENT DOCUMENTS

| KR | 10-0714464 | 5/2007 |
|---|---|---|
| KR | 10-2016-0138927 | 12/2016 |
| KR | 10-2020-0036715 | 4/2020 |

OTHER PUBLICATIONS

English Specification of 10-2020-0036715, KR.
English Specification of 10-0714464, KR.
English Specification of 10-2016-0138927, KR.

* cited by examiner

*Primary Examiner* — H. Sarah Park
(74) *Attorney, Agent, or Firm* — Antonio Ha & U.S. Patent, LLC

(57) ABSTRACT

The present disclosure relates to a functional food composition for improving muscular endurance and relieving fatigue containing *Paeoniae japonica*, *Astragalus membranaceus*, *Cnidium officinale*, velvet antler and *Platycodon grandiflorum*. Since the composition contains 6 kinds of herbal medicinal materials, the quality of the composition may be advantageously maintained, and the composition may improve muscular endurance and reduce fatigue by increasing muscle glycogen levels.

2 Claims, 3 Drawing Sheets

FUNCTIONAL FOOD COMPOSITION FOR IMPROVING MUSCULAR ENDURANCE AND RELIEVING FATIGUE

CROSS-REFERENCE TO RELATED APPLICATION(S)

This application claims priority to Korean Patent Application No. 10-2021-0018837 filed in the Korean Intellectual Property Office on Feb. 10, 2021, the disclosure of which is incorporated by reference herein in its entirety.

BACKGROUND

1. Technical Field

The present disclosure relates to a functional food composition for improving muscular endurance and relieving fatigue, and more particularly, to a functional food composition for improving muscular endurance and relieving fatigue, which may increase muscle glycogen levels, thereby improving muscular endurance and reducing fatigue, thereby enhancing exercise capacity.

2. Related Art

The effects of various natural foodstuffs on improvement in exercise performance have attracted a great deal of attention in the sports and health care industries. During physical exercise, muscle contractions release forces or power, metabolites and heat, which cause fatigue and exhaustion. Fatigue is defined as physical or emotional exhaustion that has a negative effect on endurance, exercise performance, and exercise intensity. Hard work or extreme exercise affects the production and accumulation of reactive oxygen species that increase in vivo oxidative stress levels. Extracts from various natural food sources have been studied as potential ergogenic aids that help improve exercise performance and recover from physical fatigue, and ergogenic aids such as peptides, polysaccharides, flavonoids and terpenes are based on medicinal herbs.

Muscular endurance is closely related to the improvement of athletic ability, and the deficiency thereof may lead to fatigue. Fatigue is broadly divided into mental fatigue and physical fatigue. In general, physical fatigue is defined as a state in which the force required for muscle contraction activity cannot be sufficiently exerted or maintained, or a state in which physical or mental capacity is reduced due to overwork or energy exhaustion so as not to be recovered by rest, or state in which work efficiency or exercise capacity is reduced. Known symptoms of fatigue include listless feeling, tired feeling, complete exhaustion, drowsiness, poor concentration, headache, muscle pain, etc.

Known common causes of physical fatigue include the lack of or inability to use energy sources stored in the body, the accumulation of fatigue substances such as reactive oxygen species due to metabolism, and mal-homeostasis in vivo. In particular, it has been found that reactive oxygen species are produced by metabolism, and the production thereof is further increased by excessive physical activity, excessive mental/physical stress, and the like. Meanwhile, fatigue is not caused by a single factor, but is often caused by a combination of various factors.

In order to recover from physical fatigue, sufficient energy source supply and rest, suppression and removal of the production of fatigue-related factors in vivo, etc. are required. However, in fact, sufficient nutrition and rest are not made in the busy modern society. Thus, it is required to develop a substance that can recover from or relieve fatigue.

In response to such needs, compositions for improving muscular endurance or recovering from fatigue using various kinds of natural medicinal materials have been developed. The present inventor has applied for a sports functional food as described in Patent Document 1. Specifically, Patent Document 1 discloses a sports functional food containing a herbal extract including 1 part by weight of *Paeoniae japonica*, 0.3 to 1 part by weight of jujube, 0.3 to 1 part by weight of velvet antler, 0.1 to 1 part by weight of each of *Rehmannia glutinosa*, *Astragalus membranaceus*, *Angelica gigas*, *Cnidium officinale*, *Amomum xanthioides* seed, *Achyranthes bidentata*, *Eucommia ulmoides*, *Dipsacus asperoides*, *Ophiopogon Japonicus* and ginger, 0.05 to 1 part by weight of each of cinnamon and licorice, and 0.01 to 1 part by weight of *Schizandra chinensis*. Accordingly, the sports functional food is effective not only in not only improving aerobic exercise capacity, but also in preventing and recovering from fatigue during exercise by inhibiting lactate production during exercise and promoting the decomposition of lactate generated during exercise. The sports functional food has the effect of maintaining electrolyte homeostasis. Thus, it may be effectively used as a sports functional food that can be beneficially drunk before and after various sports activities, including aerobic exercise.

In addition, Patent Document 2 discloses a composition for recovering from fatigue or enhancing exercise capacity containing an *Angelica gigas* extract, a *Cnidium officinale* extract and a *Paeoniae japonica* extract. Specifically, Patent Document 2 discloses a composition for recovering from fatigue or enhancing exercise capacity containing, as active ingredients, hot water extracts of *Angelica gigas*, *Cnidium officinale* and *Paeoniae japonica* at a weight ratio of 1:1:1, and ethanol fractions of polysaccharides thereof, wherein the hot water extracts and the ethanol fractions of polysaccharides are contained at a weight ratio of 65:35, and the composition has at least one of the following properties: i) increasing glucose levels; ii) increasing glycogen levels; iii) decreasing lactate dehydrogenase (LDH) levels; iv) decreasing malondialdehyde (MDA) levels; v) increasing glutathione peroxidase (GPx) levels; vi) increasing nuclear factor erythroid 2-related factor-2 (Nrf-2) levels; and vii) increasing heme oxygenase-1 (HO-1) expression. Accordingly, the composition can effectively relieve the fatigue accumulated in the body by controlling various factors involved in physical fatigue and/or enhancement of exercise capacity in various ways. More specifically, the composition may be effective in controlling factors related to fatigue and/or enhancement of exercise capacity by activating the Nrf-2 pathway and increasing the expression of HO-1. In addition, since the composition contains natural plant extracts or fractions thereof as active ingredients, it is completely harmless to the human body and may be effectively used with safety.

However, the composition disclosed in Patent Document 1 has problems in that it is not considered to have excellent effects despite containing many kinds of herbal medicinal materials, and it is difficult to maintain the constant supply of the herbal medicinal materials, due to a large number of kinds of herbal medicinal materials.

PRIOR ART DOCUMENTS

Patent Documents (Patent Document 1) KR 10-0714464 B1 (2007 May 4.)
(Patent Document 2) KR 10-2188238 B1 (2020 Dec. 8.)

SUMMARY

The present disclosure has been made in order to solve the above-described problems, and an object of the present disclosure is to provide a functional food composition for improving muscular endurance and relieving fatigue, which may be obtained by using a reduced number of kinds of herbal medicinal materials and further adding herbal medicinal materials capable of enhancing muscular endurance and stamina, and may enhance exercise capacity by reducing fatigue while more effectively muscular endurance.

To achieve the above object, the present disclosure provides a functional food composition for improving muscular endurance and relieving fatigue containing *Paeoniae japonica, Astragalus membranaceus, Angelica gigas, Cnidium officinale*, velvet antler and *Platycodon grandiflorum*.

In one embodiment, the *Paeoniae japonica, Astragalus membranaceus, Angelica gigas, Cnidium officinale* and velvet antler may be mixed with the *Platycodon grandiflorum* at a weight ratio of 5:1 to 2.5:1.

In one embodiment, the *Paeoniae japonica, Astragalus membranaceus, Angelica gigas, Cnidium officinale* and velvet antler are mixed together at a weight ratio of 5:4:4:4:3.

In one embodiment, the composition may further contain *Eucommia ulmoides, Dipsacus asperoides, Achyranthes bidentata Blume* and *Schizandra chinensis*.

The present disclosure also provides a method for a preparing a functional food composition for improving muscular endurance and relieving fatigue, the method comprising steps of: adding purified water to a mixture of *Paeoniae japonica, Astragalus membranaceus, Angelica gigas, Cnidium officinale*, velvet antler and *Platycodon grandiflorum*, followed by heating at a temperature of 100° C. for 2 hours; and removing solids from the mixture after the heating.

The functional food composition for improving muscular endurance and relieving fatigue according to the present disclosure contains 6 kinds of herbal medicinal materials, and thus the quality of the composition may be advantageously maintained, and the composition may improve muscular endurance and reduce fatigue by increasing muscle glycogen levels.

DETAILED DESCRIPTION

Figure 1:
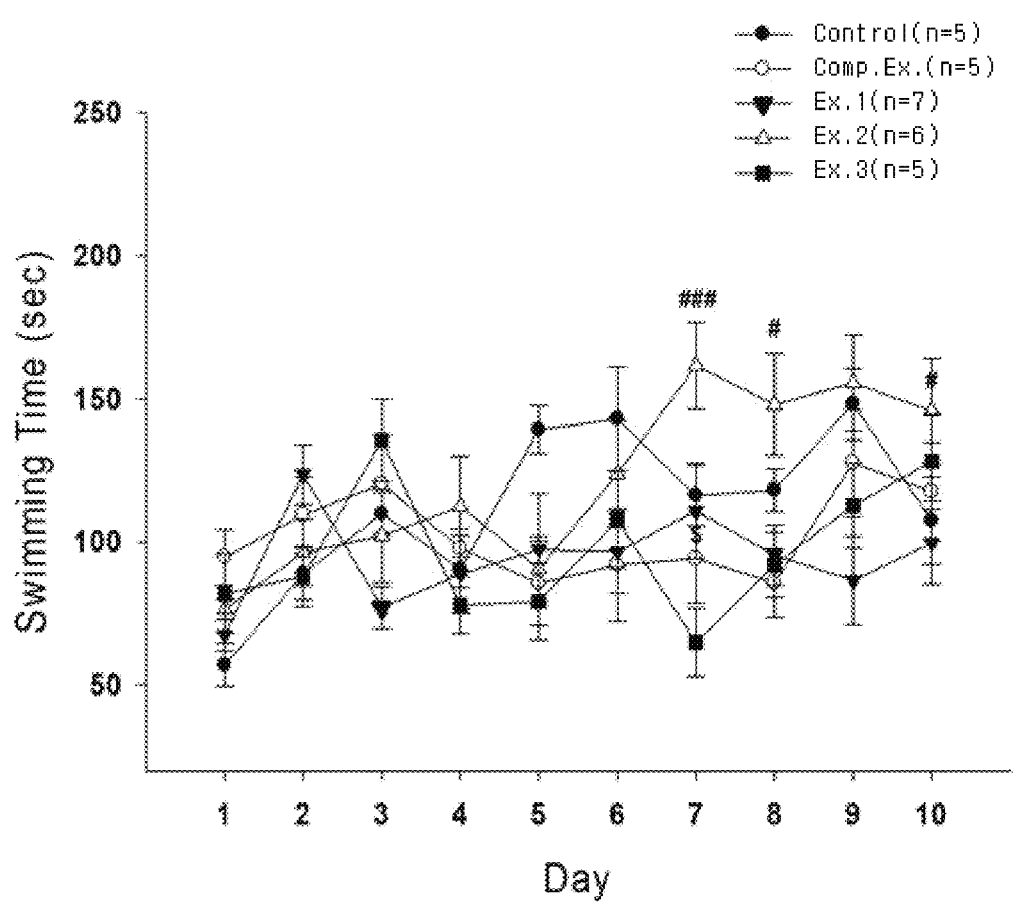
FIG. 1 is a graph showing the effects of herbal extracts on the forced swimming capacity of rats.

The terms and words used in the specification and claims should not be interpreted as being limited to typical meanings or dictionary definitions, but should be interpreted as having meanings and concepts relevant to the technical scope of the present disclosure, based on the principle that the inventors can appropriately define the meaning of the terms to describe their invention in the best manner.

Accordingly, it should be understood that the embodiments and experimental examples described in the specification are merely preferred examples, but not cover all the technical spirits of the present invention, and thus there may be various equivalents and modifications capable of replacing them at the time of filing of the present disclosure.

The composition according to the present disclosure may be a pharmaceutical composition.

Solid formulations for oral administration include tablets, pills, powders, granules and capsules. These formulations may be prepared by mixing the extract of the present disclosure with one or more excipients, for example, starch, calcium carbonate, sucrose, lactose and gelatin. In addition to simple excipients, lubricants such as magnesium stearate and talc may also be used.

Liquid formulations for oral administration include suspensions, liquids, solutions, emulsions, and syrups. These formulations may contain various excipients, such as a wetting agent, a sweetener, fragrance, and a preservative, in addition to commonly used simple diluents such as water and liquid paraffin.

In addition, the composition according to the present disclosure may be a food composition. Examples of the food composition include various foods, beverages, gums, teas, and vitamin complexes.

In particular, when the composition is used as a functional beverage, it may contain various flavoring agents or natural carbohydrates as additional ingredients.

Examples of the natural carbohydrates include conventional sugars, such as monosaccharides (e.g., glucose, fructose, etc.), disaccharides (e.g., maltose, sucrose, etc.), polysaccharides (e.g., dextrin, cyclodextrin, etc.), and sugar alcohols such as xylitol, sorbitol, erythritol or the like. In addition, examples of flavoring agents that may be advantageously used in the present disclosure include natural flavoring agents (thaumatin, *stevia* extracts, such as rebaudioside A, glycyrrhizin, etc.) and synthetic flavoring agents (saccharin, aspartame, etc.).

In addition, the composition of the present disclosure may further contain various nutrients, vitamins, minerals (electrolytes), flavoring agents such as synthetic flavoring agents and natural flavoring agents, colorants, extenders (cheese, chocolate, etc.), pectic acid and its salt, organic acids, protective colloidal thickeners, pH adjusting agents, stabilizers, preservatives, glycerin, alcohol, carbonizing agents used in carbonated beverages, etc.

Example 1

250 ml of purified water was added to 48 g of an herbal mixture consisting of 10 g of *Paeoniae japonica*, 8 g of *Astragalus membranaceus* (4 years old), 8 g of *Angelica gigas*, 8 g of *Cnidium officinale*, 6 g of velvet antler, and 8 g of *Platycodon grandiflorum* (3 years old). Next, the mixture was heated at a temperature of 100° C. for 2 hours, and then solids were removed therefrom, thus obtaining 100 ml of an extract.

Example 2

250 ml of purified water was added to 49 g of an herbal mixture consisting of 8.75 g of *Paeoniae japonica*, 7 g of *Astragalus membranaceus* (4 years old), 7 g of *Angelica gigas*, 7 g of *Cnidium officinale*, 5.25 g of velvet antler, and 14 g of *Platycodon grandiflorum* (3 years old). Next, the mixture was heated at a temperature of 100° C. for 2 hours, and then solids were removed therefrom, thus obtaining 100 ml of an extract.

Example 3

370 ml of purified water was added to 74 g of an herbal mixture consisting of 12 g of *Paeoniae japonica*, 10 g of *Astragalus membranaceus* (4 years old), 10 g of *Angelica gigas*, 10 g of *Cnidium officinale*, 8 g of velvet antler, 8 g of *Platycodon grandiflorum* (3 years old), 4 g of *Eucommia ulmoides*, 4 g of *Dipsacus asperoides*, 4 g of *Achyranthes bidentata* Blume and 4 g of *Schizandra chinensis*. Next, the mixture was heated at a temperature of 100° C. for 2 hours, and then solids were removed therefrom, thus obtaining 100 ml of an extract.

Comparative Example 250 ml of purified water was added to 50 g of an herbal mixture consisting of 12 g of *Paeoniae japonica*, 10 g of *Astragalus membranaceus* (4 years old), 10 g of *Angelica gigas*, 10 g of *Cnidium officinale*, and 8 g of velvet antler. Next, the mixture was heated at a temperature of 100° C. for 2 hours, and then solids were removed therefrom, thus obtaining 100 ml of an extract.

Results obtained in the following experimental examples are expressed as mean±SEM and analyzed by t-test or post-hoc test using two-way analysis of variance (ANOVA) and Tukey's method. Statistical significance was considered at $p \leq 0.05$.

Experimental Example 1. Animal Test Preparation

Adult male Sprague-Dawley rats (weighing 270 to 320 g) were obtained from Central Lab Animal Inc. (Seoul). The rats were housed at room temperature (22±2° C.) with a 12-hr light/12-hr dark cycle (turned on at 07:00 AM). All animals were treated according to the regulations of the Daegu Haany University Institutional Animal Care and Use Committee.

Experimental Example 2. Forced Swimming Test 2-1. Test Preparation

Each rat was housed in a plastic container (30×30×80 cm) filled with fresh water at a temperature of 25±5° C. The container was about 60 cm in deep so that each rat could not support itself by letting its tail touch the bottom. A glass rod (10% of body weight) was placed on the proximal part of the rat's tail. At the end of the swimming session, the rat was taken out of the container, dried with a paper towel, and placed again in the container. Total swimming time was calculated as the time from falling into the water to the state of complete exhaustion evidenced by drowning.

2-2. Test Results

|  | Control | Comparative Example | Example 1 | Example 2 | Example 3 |
|---|---|---|---|---|---|
| Day 1 | 57.00 | 89.40 | 67.57 | 68.33 | 82.00 |
| Day 2 | 88.86 | 120.00 | 123.57 | 95.00 | 88.00 |
| Day 3 | 109.86 | 133.00 | 77.14 | 116.33 | 135.60 |
| Day 4 | 90.57 | 110.60 | 88.71 | 114.50 | 78.00 |
| Day 5 | 139.29 | 98.00 | 97.43 | 93.17 | 79.20 |
| Day 6 | 143.14 | 97.40 | 96.57 | 123.00 | 107.80 |
| Day 7 | 116.14 | 101.00 | 110.86 | 162.27 | 65.00 |
| Day 8 | 118.14 | 98.20 | 95.43 | 156.17 | 92.00 |
| Day 9 | 162.57 | 159.00 | 86.57 | 159.67 | 112.80 |
| Day 10 | 78.86 | 114.20 | 99.71 | 168.33 | 139.20 |

Unit: seconds

The test results are shown in Table 1 above and FIG. 1. Referring thereto, in the case of Example 2, the swimming time tended to increase gradually until day 6, and then increased by about 30% or more on day 7 compared to day 6, and then this level was maintained. On the other hand, in the case of the Comparative Example, the forced swimming time increased on day 2, but the swimming time decreased from day 4 and tended to maintain the decreased state. It was confirmed that, in the case of Example 1, the swimming time increased compared to day 1, but this increase was not significant compared to that in the Comparative Example. In addition, even in the case of Example 3, similar results were obtained. Thereby, it can be seen that the swimming time of the rats to which the extract according to Example 2 was administered was the longest, suggesting that the endurance of these rats was enhanced.

Experimental Example 3. Analysis of Tissue Glycogen Level 3-1. Experiment Preparation After serum was collected, the liver and soleus muscle were dissected rapidly, frozen in liquid nitrogen, and stored at −80° C. until analysis. Each sample was boiled in 2.0 M HCl at a temperature of 100° C. for 1 hour. After brief centrifugation, each sample was neutralized with 2.0 M NaOH into a hydrolysis product, and centrifuged again at 3000 rpm for 10 minutes. Glycogen levels were measured using a chemical analyzer (VetTest 8008, MEDEXX, Korea).

3-2. Experimental Results

When a large amount of glycogen is consumed, the body's ability to move is reduced. When physical fatigue accumulates, it causes a lack of energy during exercise. In particular, the main starting material for glycolysis is glycogen stored in the liver and muscles. The glycogen is classified as a usable resource for energy production, and the amount thereof directly affects exercise capacity. As the amount of glycogen stored increases, exercise capacity may be enhanced and the occurrence of exercise fatigue may be delayed.

Figure 2:
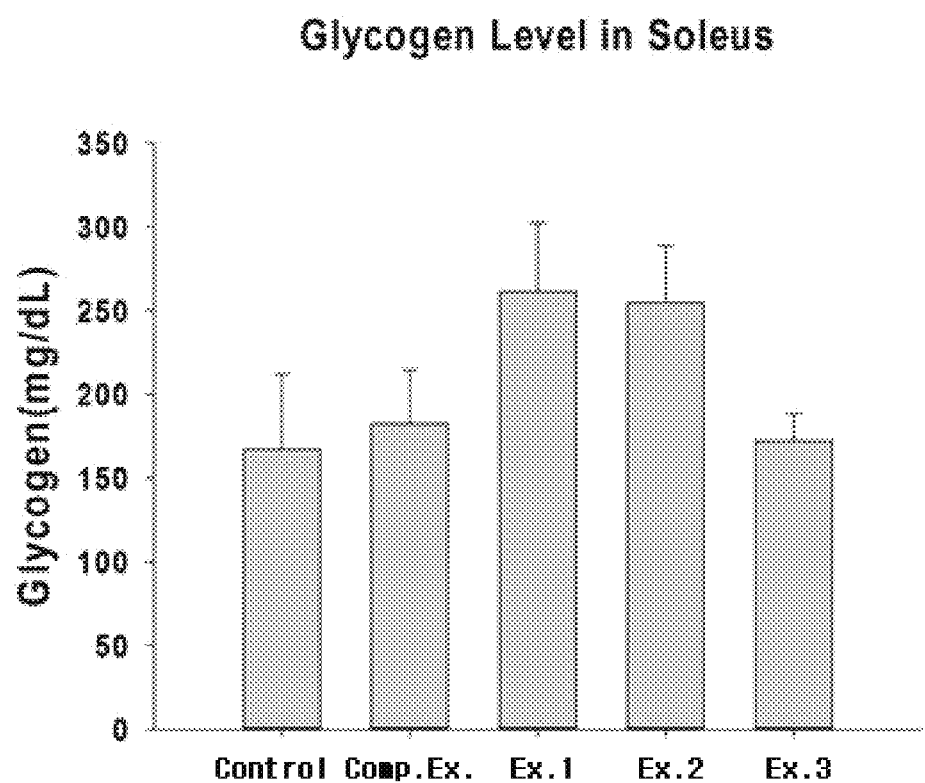
FIG. 2 is a graph showing the effects of herbal extracts on glycogen levels in soleus after a forced swimming test.

Referring to FIG. 2, it was confirmed that, the intracellular glycogen levels for Examples 1 and 2 increased by about 87% and about 80%, respectively, compared to that for the control, and increased by about 47% and about 40%, respectively, compared to that for the Comparative Example. Thereby, it can be seen that the extracts of Examples 1 and 2 reduce muscle fatigue and enhance exercise capacity by increasing the content of glycogen in the soleus muscle, thereby improving muscular endurance.

Example 4. Analysis of Blood Biochemical Parameters 4-1. Experiment Preparation

Blood was collected from the thoracoabdominal aorta under isoflurane anesthesia and centrifuged at 3000 rpm at 4° C. for 10 min to obtain serum which was then stored at −80° C. in a cryogenic freezer. BUN levels were measured using a chemical analyzer (VetTest 8008, MEDEXX, Korea).

4-2. Experimental Results

Figure 3:
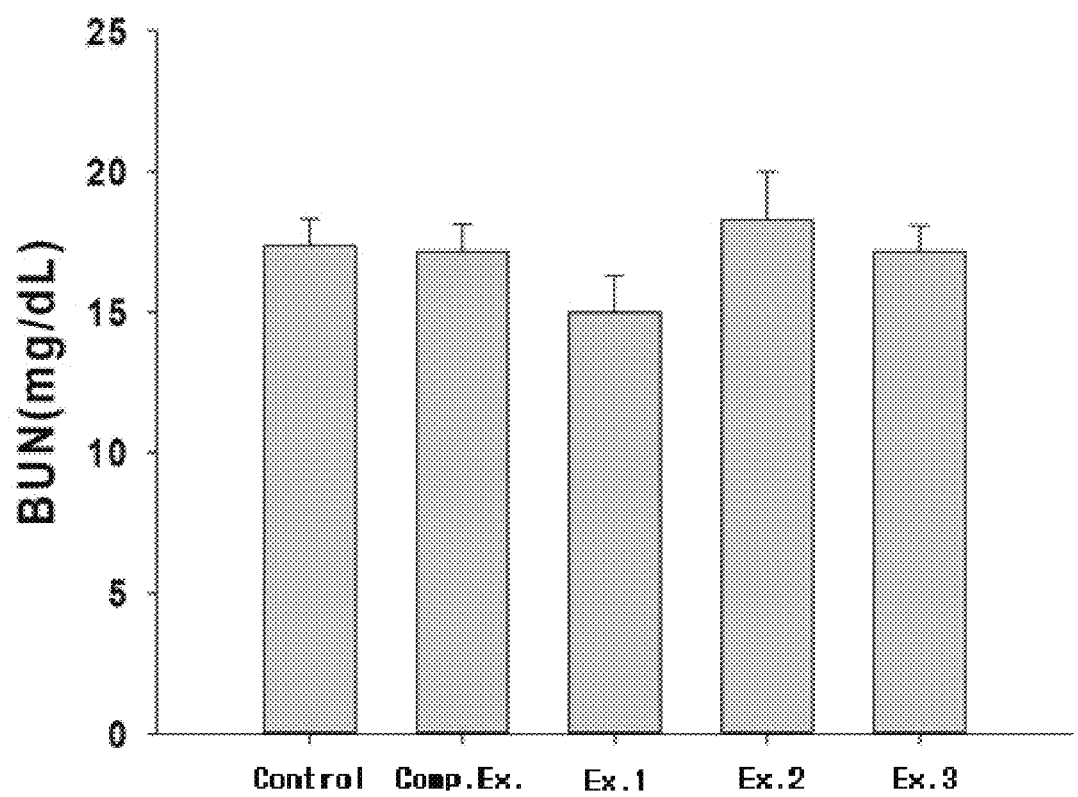
FIG. 3 is a graph showing the effects of herbal extracts on BUN levels in serum after a forced swimming test.

Urea is a waste product produced when protein is broken down in the liver, and it reaches the kidneys through the blood and is excreted in the urine. Most of the urea produced in the body is removed by the kidneys, and thus the kidney function may be checked by checking the blood urea nitrogen level. As shown in FIG. 3, it was confirmed that there was no significant difference in the blood urea nitrogen (BUN) level between Examples 1 to 3, suggesting that the functional food composition for improving muscular endurance and relieving fatigue according to the present disclosure is safe for the kidneys.

What is claimed is:

1. A functional food composition for improving muscular endurance and relieving fatigue containing an extract of a mixture of *Paeoniae japonica, Astragalus membranaceus, Angelica gigas, Cnidium officinale*, velvet antler and *Platycodon grandiflorum*,
    wherein the *Paeoniae japonica, Astragalus membranaceus, Angelica gigas, Cnidium officinale* and velvet antler are mixed with the *Platycodon grandiflorum* at a weight ratio of 5:1 to 2.5:1, and
    the *Paeoniae japonica, Astragalus membranaceus, Angelica gigas, Cnidium officinale* and velvet antler are mixed together at a weight ratio of 5:4:4:4:3.

2. A method for preparing the functional food composition for improving muscular endurance and relieving fatigue according to claim 1, the method comprising steps of:
    adding purified water to a mixture of *Paeoniae japonica, Astragalus membranaceus, Angelica gigas, Cnidium officinale*, velvet antler and *Platycodon grandiflorum*, followed by heating at a temperature of 100° C. for 2 hours; and removing solids from the mixture after the heating.

* * * * *